(12) United States Patent
Doi et al.

(10) Patent No.: US 8,492,105 B2
(45) Date of Patent: Jul. 23, 2013

(54) SCREENING METHOD FOR AN INSULIN RESISTANCE IMPROVING AGENT OR A THERAPEUTIC AGENT FOR DIABETES

(75) Inventors: Kentarou Doi, Kawasaki (JP);
Takayoshi Kinoshita, Osaka (JP);
Atsushi Tomonaga, Kawasaki (JP);
Hajime Sugiyama, Kawasaki (JP);
Matsuyo Wada, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 13/618,417

(22) Filed: Sep. 14, 2012

(65) Prior Publication Data

US 2013/0022993 A1 Jan. 24, 2013

Related U.S. Application Data

(60) Division of application No. 13/214,712, filed on Aug. 22, 2011, now Pat. No. 8,354,373, which is a continuation of application No. PCT/JP2010/052765, filed on Feb. 23, 2010.

(30) Foreign Application Priority Data

Feb. 23, 2009 (JP) ................................ 2009-039997

(51) Int. Cl.
*G01N 33/53* (2006.01)
(52) U.S. Cl.
USPC .......................................................... 435/7.1
(58) Field of Classification Search
USPC .......................................................... 435/7.1
See application file for complete search history.

(56) References Cited

U.S. PATENT DOCUMENTS 6,369,198 B1 4/2002 Serlupi-Crescenzi et al.

FOREIGN PATENT DOCUMENTS

JP 3-11097 A 1/1991
WO 2004/094605 A2 11/2004

OTHER PUBLICATIONS

Extended European Search Report dated Jul. 11, 2012, issued in corresponding European Patent Application No. 10743876.4, (10 pages).
Andersson, et al., "Insulin antagonizes interleukin-6 signaling and is anti-inflammatory in 3T3-L1 adipocytes", Journal of Biological Chemistry, dated Mar. 2007, vol. 282, No. 13, pp. 9430-9435, XP002678567. Cited in Extended European Search Report dated Jul. 11, 2012.
Lu, et al., "STAT-3 and ERK 1/2 phosphorylation are critical for T-cell alloactivation and graft-versus-host disease", Blood, dated Dec. 2008, vol. 112, No. 13, pp. 5254-5258, XP002678568. Cited in Extended European Search Report dated Jul. 11, 2012.
Vinciguerra, et al., "Differential phosphorylation of c-Jun and JunD in response to the epidermal growth factor is determined by the structure of MAPK targetting sequences", Journal of Biological Chemistry, vol. 279, No. 10, dated Mar. 5, 2004, pp. 9634-9641, XP002678569. Cited in Extended European Search Report dated Jul. 11, 2012.
Inoue, et al., "Role of hepatic STAT3 in brain-insulin action on hepatic glucose production", Cell Metabolism, dated Apr. 2006, vol. 3, No. 4, pp. 267-275, XP002678673. Cited in Extended European Search Report dated Jul. 11, 2012.
International Search Report of PCT/JP2010/052765, mailing date Mar. 30, 2010.
Chung J et al., "STAT3 Serine Phosphorylation by ERK-Dependent and—Independent Pathways Negatively Modulates Its Tyrosine Phosphorylation", Molecular and Cellular Biology, vol. 17, No. 11, Nov. 1997, p. 6508-6516.
Decker, T et al., "Serine phosphorylation of STATs"; Oncogene, (2000), vol. 19, p. 2628-2637.
Inoue, Kei et al., "Information network between organs via IL-6/STAT3 and glucose metabolism regulation"; Himan Kenkyu, 22, Sep. 2008, vol. 14 (Supplement), p. 94.
Inoue, Hiroshi et al., "Double Control of Hapatic Gluconeogenesis by Insulin"; Bunshi Tonyobyogaku no Shinpo-Kiso Kara Rinsho made-2007, Kanehara & Co., Ltd., 2007, p. 28-35.
Inoue, Hiroshi et al., "Importance of STAT3 in controlling glucose metabolism in the liver", BIO. Clinica, 2004, vol. 19, No. 7, pp. 48-53.
Inoue, Hiroshi et al., "Role of STAT-3 in regulation of hepatic gluconeogenic genes and carbohydrate metabolism in vivo"., Nature Medicine, vol. 10, No. 2, Feb. 2004, pp. 168-174.
Jain N. et al "Repression of STAT 3 activity by activation of mitogen-activated protein kinase (MAPK)", Oncogene (1998), vol. 17, No. 24, pp. 3157-3167.
Kanauchi M. "A new index of insulin sensitivity obtained from the oral glucose tolerance test applicable to advanced type 2 diabetes", Diabetes Care, 2002, vol. 25, No. 10, pp. 1891-1892.
Kim J. H. et al., "Signal transducer and Activator of Transcription 3 (STAT3) Mediates Amino Acid Inhibition of Insulin Signaling through Serine 727 Phosphorylation", The Journal of Biological Chemistry, vol. 284, No. 51, pp. 35425-35432, 2009.
Kim J. H. et al "Regulation of Interleukin-6-induced Hepatic Insulin Resistance by Mammalian Target of Rapamycin through the STAT3-SOCS3 Pathway", The Journal of Biological Chemistry 2008, vol. 283, No. 2, pp. 708-715.
Ueki, Kojiro "Impairment of insulin action by proinflammatory cytokine-induced SOCS proteins", Diabetes Journal, vol. 32, No. 4, 2004, pp. 28-29.

(Continued)

*Primary Examiner* — Gyan Chandra
(74) *Attorney, Agent, or Firm* — Westerman, Hattori, Daniels & Adrian, LLP

(57) ABSTRACT

A new compound inhibiting phosphorylation of Ser727 of STAT3, a phosphorylation inhibitor containing the new compound, an insulin resistance improving agent and a preventive or therapeutic agent for diabetes; and a screening method for at least one of the insulin resistance improving agent and the preventive or therapeutic agent for diabetes.

6 Claims, 4 Drawing Sheets

OTHER PUBLICATIONS

Liu S et al., "Structural basis of docking interactions between ERK2 and MAP kinase phosphatase 3", Proc. Natl. Acad Sci. USA, vol. 103, No. 14, 2002, pp. 5326-5331.

Kasuga, Masato "Impairment of Insulin Signal Transduction in Development of Diabetes", Nihon Naika Gakkai Zasshi, vol. 96, No. 9, 2007, pp. 36-44.

Matthews D.R. et al., "Homeostasis model assessment:insulin resistance and β-cell function from fasting plasma glucose and insulin concentration in man", Diabetologis., 1985, vol. 28, No. 7, pp. 412-419.

Ogawa, Wataru et al., "Roles of Liver STAT3 in Glucose Metabolism"., Annual Review Nai bunpitsu, Taisha 2005, Kabushiki Kaisha Chuo Igakusha, Jan. 20, 2005, pp. 38-43.

Ogawa, Wataru "Control of Hepatic Gluconeogenesis by Insulin", Tonyobyogaku no Shinpo, (vol. 40) 2006, Kabushiki Kaisha Shindan to Chiryosha, 2006, pp. 180-186.

Ogawa, Wataru "IL-6/IL-6 Receptor and Diabetes", Diabetes Frontier, 2008, vol. 19, No. 4, pp. 509-513.

Ogawa, Wataru "Interleukin-6 and glucose metabolism", Igaku no Ayumi, 2006, vol. 219, No. 6, pp. 463-466.

Nakajima, Koichi "Recent Advancements on Kinasa System controlling STAT3 Ser727 Phosphorylation and Studies of Roles thereof" Annual Review Man'eki 2006, Kabushiki Kaisha Chugai Igakusha, 2005, pp. 126-133.

Ueki K et al., "Role of suppressors of cytokine signaling SOCS-1 and SOCS-3 in hepatic steatosis and the metabolic syndrome", Hapatal Res., 2005, vol. 33, No. 2, pp. 185-192.

Postprandial blood glucose level

Fasting blood insulin level

Increment in fasting blood insulin level

SEQUENCE LISTING

```
<160> NUMBER OF SEQ ID NOS: 1

<210> SEQ ID NO 1
<211> LENGTH: 7
<212> TYPE: PRT
<213> ORGANISM: artificial sequence
<220> FEATURE:
<223> OTHER INFORMATION: Description of Artificial Sequence: Synthetic
      sequence

<400> SEQUENCE: 1

Lys Lys Tyr Ile Leu Ala Leu
1               5
```

SCREENING METHOD FOR AN INSULIN RESISTANCE IMPROVING AGENT OR A THERAPEUTIC AGENT FOR DIABETES

CROSS-REFERENCE TO RELATED APPLICATION

This application is a divisional of U.S. application Ser. No. 13/214,712, filed on Aug. 22, 2011, which in turn is a continuation application of PCT/JP2010/052765, filed on Feb. 23, 2010, and which claims priority from Japanese patent application No. 2009-039997, filed Feb. 23, 2009, the entire contents of which are incorporated herein by reference.

FIELD

The embodiments discussed herein relate to a new compound having an inhibitory activity against phosphorylation of Ser727 of STAT3, a phosphorylation inhibitor containing the new compound, an insulin resistance improving agent, a preventive or therapeutic agent for diabetes, and an efficient screening method for at least one of the insulin resistance improving agent and the preventive or therapeutic agent for diabetes.

BACKGROUND

The blood glucose level is constantly controlled so as to fall within a certain range at a normal state. A peptide hormone called insulin is important for controlling the blood glucose level. This peptide hormone is excreted from 13 cells of islets of Langerhans present in the pancreas. When the insulin binds to an insulin receptor present on the cell membrane, various signal transductions occur to suppress gluconeogenesis, leading to a drop in the blood glucose level.

The reason why the blood glucose level is controlled is that glucose serves as a harmful substance causing glycosylation stress in tissue although it is a main energy source for organs including the brain.

When the control ability of the blood glucose level (glucose tolerance) is decreased, one is in a state where the blood glucose level has pathologically increased or a state where the blood glucose level potentially increases. Such a state that the glucose metabolism has been abnormal is diabetes.

The diabetes is classified into type 1 diabetes (insulin-dependent diabetes) and type 2 diabetes (insulin-independent diabetes). The type 2 diabetes, most of the diabetes belong to, is further classified into diabetes caused due to a decrease in the level of excreted insulin and diabetes in which although insulin is excreted at a sufficiently high level, the blood glucose level does not decrease due to reduction in insulin susceptibility of glucose in the target cells. The latter case is called insulin resistance.

The current diabetes therapy is conducted using various drugs selected depending on the pathological conditions. The types of the drugs are classified roughly into insulin, an insulin-excretion promoter, a glucose absorption inhibitor and an insulin resistance improving agent.

For patients exhibiting the above-described insulin resistance, an insulin resistance improving agent such as metformin hydrochloride, buformine hydrochloride or pioglitazone hydrochloride is used as the first-line drug. However, such an insulin resistance improving agent involves gastrointestinal disorder as side effects. In addition, it cannot be applied to those having a history of heart failure. Also, pioglitazone hydrochloride involves increase in body weight as side effects, which imposes problematic burden on patients who are receiving dietary therapy.

Meanwhile, besides insulin, signal transducer and activator of transcription 3 (STAT3) has recently been reported as a factor that decreases the blood glucose level (see Inoue H et al., Nat Med, 10(2), 2004, p. 168-74).

The STAT3 is a protein that works for both of signal transduction and transcription activation, and controls processes such as cell growth, differentiation and survival. The STAT3 exists in the cytoplasm in the non-phosphorylated form. When the STAT3 is activated by Janus kinase (JAK) so that its Tyr705 is phosphorylated, a homodimer of the STAT3 is formed and transferred into the nucleus, where it serves as a transcriptional factor to activate the target gene.

The homodimer of the STAT3 serves in the nucleus as an antagonist against a transcriptional factor responsible for gluconeogenesis. Increase in the expression level thereof suppresses gluconeogenesis to reduce the blood glucose level.

Also, as has been known, when Ser727 of the STAT3 is phosphorylated by extracellular signal-regulated kinase 2 (ERK2), formation of the homodimer of the STAT3 is inhibited (see Chung J et al., Mol Cell Biol, 17(11), 1997, p. 6508-16; Jain N et al., Oncogene, 17(24), 1998, p. 3157-67; and Liu S et al., Proc Natl Acad Sci USA, 103(14), 2006, p. 5326-31).

However, diabetes therapeutic drugs relating to the STAT3 have not been known.

Thus, in the prevention or therapy for diabetes, there have not yet been provided an effective, safe drug having a target molecule and mechanism which are different from those of these existing drugs, and an efficient screening method for a candidate substance of the above drug. At present, keen demand has arisen for the provision of them.

SUMMARY

According to an aspect of an embodiment, a compound inhibits phosphorylation of Ser727 of STAT3.

According to another aspect of an embodiment, a phosphorylation inhibitor contains the above compound.

According to still another aspect of an embodiment, an insulin resistance improving agent contains the above phosphorylation inhibitor.

According to yet another aspect of an embodiment, a preventive or therapeutic agent for diabetes contains the above insulin resistance improving agent.

According to even another aspect of an embodiment, a screening method for at least one of the insulin resistance improving agent and the preventive or therapeutic agent for diabetes includes determining the presence or absence of at least interaction between STAT3 and ERK2 to select a compound having a phosphorylation inhibitory activity and evaluating the compound for whether X>Y where X denotes a HOMA-IR value of a diabetes model animal to which the compound has not been administered and Y denotes a HOMA-IR value of a diabetes model animal to which the compound has been administered.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS (New Compound)

Figure 1:
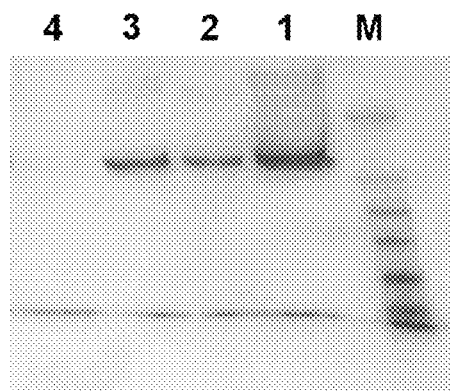
FIG. 1 indicates the results of a phosphorylation inhibitory activity test performed by western blotting.

The disclosed new compound inhibits phosphorylation of Ser727 of the STAT3.

The STAT3 has several phosphorylation sites. For example, when its Ser727 is phosphorylated, the STAT3 cannot form its homodimer to be transferred into the nucleus. Thus, it cannot serve as a transcriptional factor.

The Ser727 of the STAT3 is phosphorylated by ERK2, for example. Specifically, the ERK2 is activated through phosphorylation of its Tyr185 by MAPK/ERK kinase 1 (MEK1) and then binds to the STAT3 to form a heterodimer, where the Ser727 of the STAT3 is phosphorylated.

Thus, when the phosphorylation of the Ser727 is inhibited by the above phosphorylation inhibitor, the STAT3 is not prevented from forming its homodimer and the formed homodimer of the STAT3 can serve as a transcriptional factor.

<New Compound Containing Peptide Represented by Amino Acid Sequence Structure (I)>

The above new compound contains at least a peptide represented by the following amino acid sequence structure (I), for example.

—Peptide Represented by Amino Acid Sequence Structure (I)—

The peptide represented by the amino acid sequence structure (I) is as follows.

$\alpha$-$\alpha'$-$\beta$-$\gamma$-$\delta'$-$\sigma$-$\delta$ . . . Amino acid sequence structure (I)

The peptide represented by the amino acid sequence structure (I) is preferably at least one of peptides represented by the following amino acid sequence structures (II) and (III).

Lys-Lys-$\beta$-$\gamma$-$\delta'$-$\sigma$-$\delta$ . . . Amino acid sequence structure (II)

$\alpha$-$\alpha'$-$\beta$-$\gamma$-Leu-$\sigma$-Leu . . . Amino acid sequence structure (III)

In the amino acid sequence structures (I), (II) and (III), $\alpha$ denotes an N terminus, $\delta$ denotes a C terminus, $\alpha$ and $\alpha'$ each denote lysine or arginine, $\delta$ and $\delta'$ each denote leucine or isoleucine, and $\beta$, $\gamma$ and $\sigma$ each denote any amino acid.

The amino acid denoted by $\beta$ is not particularly limited and may be appropriately selected depending on the intended purpose. It is preferably tyrosine.

The amino acid denoted by $\gamma$ is not particularly limited and may be appropriately selected depending on the intended purpose. It is preferably isoleucine.

The amino acid denoted by $\sigma$ is not particularly limited and may be appropriately selected depending on the intended purpose. It is preferably alanine.

Among the peptides represented by the amino acid sequence structures (I), (II) and (III), more preferred is a peptide containing an amino acid sequence expressed by the following SEQ ID No. 1. Particularly preferably is a peptide itself expressed by the following SEQ ID No. 1.

```
                                           (SEQ ID No. 1)
        Lys-Lys-Tyr-Ile-Leu-Ala-Leu
```

So long as the above new compound has an inhibitory activity against phosphorylation of the Ser727 of the STAT3, the above peptide may have an amino acid sequence expressed by the above SEQ ID No. 1 in all or part of which one to several amino acids have been substituted or added. Also, the peptide may be chemically modified at its N or C terminus. This chemical modification is not particularly limited and may be appropriately selected depending on the intended purpose. Examples thereof include acetylation, myristoylation and amidation.

The amount of the peptide represented by the above amino acid sequence structure (I) contained in the new compound is not particularly limited and may be appropriately selected depending on the intended purpose. Also, the new compound may be the peptide itself represented by the above amino acid sequence structure (I).

The method for obtaining the peptide is not particularly limited and may be appropriately selected depending on the intended purpose. Examples thereof include a method in which the peptide is obtained as a synthetic peptide produced through chemical synthesis.

The method for chemically synthesizing the peptide is not particularly limited and may be appropriately selected depending on the intended purpose. Examples thereof include a method in which the peptide is chemically synthesized using a peptide synthesizer (product of Shimadzu Corporation).

The above new compound may be in the form of salt. The salt is not particularly limited and may be appropriately selected depending on the intended purpose. Examples thereof include carboxylates, inorganic acid salts, amino acid salts and sulfonates.

Examples of the carboxylates include trifluoroacetate, acetate, trichloroacetate, hydroxyacetate, lactate, citrate, tartarate, oxalate, benzoate, butyrate, maleate, propionate, formate and malate.

Examples of the inorganic acid salts include hydrohalic acid salts, sulfate, nitrate, phosphate and carbonate.

Examples of the amino acid salts include alginate, aspartate and glutamate.

Examples of the sulfonates include methanesulfonate and p-toluenesulfonate.

(Phosphorylation Inhibitor)

The disclosed phosphorylation inhibitor contains at least the above-described new compound or a salt thereof; and, if necessary, further contains other ingredients.

The amount of the new compound or a salt thereof contained the above phosphorylation inhibitor is not particularly limited and may be appropriately selected depending on the intended purpose. Also, the phosphorylation inhibitor is the new compound or a salt thereof itself.

<Other Ingredients>

The other ingredients contained in the phosphorylation inhibitor are not particularly limited and may be appropriately selected depending on the intended purpose. Examples thereof include pharmacologically acceptable carriers.

The above carriers are not particularly limited and may be appropriately selected depending on, for example, the dosage form of the phosphorylation inhibitor.

The amount of the other ingredients contained in the phosphorylation inhibitor is not particularly limited and may be appropriately selected depending on the intended purpose.

<Measurement Method for Phosphorylation Inhibitory Activity>

The measurement method for the phosphorylation inhibitory activity is not particularly limited and may be appropriately selected depending on the intended purpose. Examples thereof include immunoassay.

The immunoassay is not particularly limited and may be appropriately selected depending on the intended purpose. Examples thereof include immunostaining, immunoprecipitation, western blotting and ELISA, with western blotting being preferred.

<Application>

The application of the phosphorylation inhibitor is not particularly limited and can suitably used as a drug such as the below-described insulin resistance improving agent or preventive or therapeutic agent for diabetes. Also, the phosphorylation inhibitor can be used as, for example, a reagent for assay using phosphorylation as an index.

When the phosphorylation inhibitor is used as a reagent, the method for using it is not particularly limited and may be appropriately selected depending on the intended purpose. For example, the phosphorylation inhibitor may be added to a culture liquid of culture cells.

(Insulin Resistance Improving Agent and Preventive or Therapeutic Agent for Diabetes)

<Insulin Resistance Improving Agent>

The disclosed insulin resistance improving agent contains at least the above-described phosphorylation inhibitor; and, if necessary, further contains other ingredients.

The amount of the phosphorylation inhibitor contained in the insulin resistance improving agent is not particularly limited and may be appropriately selected depending on the intended purpose. Also, the insulin resistance improving agent may be the phosphorylation inhibitor itself.

—Evaluation of Insulin Resistance—

The method for evaluating whether the insulin resistance improving agent improves insulin resistance is not particularly limited and may be appropriately selected depending on the intended purpose. Preferred is a method of evaluating it using the HOMA-IR (homeostasis model assessment) method. The HOMA-IR method is a method of calculating a HOMA-IR value serving as an index of insulin resistance using the following calculation formula.

HOMA-IR (index of insulin resistance)=fasting insulin level (µU/mL)×fasting blood glucose level (mmol/L)/22.5

This evaluation is based on that the lower the HOMA-IR value is, the more improved the insulin resistance is (see Matthews D R et al., Diabetologia 1985 July 28(7), 412-9, Kanauchi M et al., Diabetes Care, October 25(10), 2002, p. 1891-2).

The fasting is not particularly limited and may be appropriately selected depending on the intended purpose. It is preferably 12 hours to 14 hours after eating.

The method for obtaining a blood sample used for measuring the fasting insulin level and the fasting blood glucose level is not particularly limited. The blood sample can be obtained by routinely-used blood sampling. The blood sample is not particularly limited and may be appropriately selected depending on the intended purpose. It is preferably a serum. The method for preparing the serum is not particularly limited and may be appropriately selected depending on the intended purpose. Examples thereof include a method in which the sampled blood is centrifuged.

The method for determining the fasting insulin level is not particularly limited and may be appropriately selected depending on the intended purpose. Examples thereof include a method in which the fasting insulin level is determined using a mouse insulin ELISA kit (Cat. #EZRMI-13K, product of Linco Research Inc.).

The method for determining the fasting blood glucose level is not particularly limited and may be appropriately selected depending on the intended purpose. Examples thereof include a method in which the fasting blood glucose level is determined using Johnson one-touch Ultra Glucose Monitoring System (product of Johnson & Johnson K.K.).

—Application—

As to the application of the insulin resistance improving agent, the insulin resistance improving agent can suitably used as a drug such as the below-described preventive or therapeutic agent for diabetes.

<Preventive or Therapeutic Agent for Diabetes>

The disclosed preventive or therapeutic agent for diabetes contains at least the insulin resistance improving agent; and, if necessary, further contains other ingredients.

The amount of the insulin resistance improving agent contained in the preventive or therapeutic agent for diabetes is not particularly limited and may be appropriately selected depending on the intended purpose. Also, the preventive or therapeutic agent for diabetes may be the insulin resistance improving agent itself.

<Other Ingredients>

The other ingredients contained in the insulin resistance improving agent or the preventive or therapeutic agent for diabetes are not particularly limited and may be appropriately selected depending on the intended purpose. Examples thereof include pharmacologically acceptable carriers.

The above carriers are not particularly limited and may be appropriately selected depending on, for example, the dosage form of the phosphorylation inhibitor, the insulin resistance improving agent or the preventive or therapeutic agent for diabetes.

The amount of the other ingredients contained in the insulin resistance improving agent or the preventive or therapeutic agent for diabetes is not particularly limited and may be appropriately selected depending on the intended purpose.
(Use)

The phosphorylation inhibitor, the insulin resistance improving agent, and the preventive or therapeutic agent for diabetes may be used alone or in combination. Also, they are used in combination with a drug containing other active ingredients. Furthermore, the phosphorylation inhibitor, the insulin resistance improving agent, and the preventive or therapeutic agent for diabetes may be formulated into a drug containing other active ingredients before use.
(Dosage Form)

The dosage form of the phosphorylation inhibitor, the insulin resistance improving agent, or the preventive or therapeutic agent for diabetes is not particularly limited and may be appropriately selected depending on a desired administration method. Examples thereof include an oral solid preparation, an oral liquid preparation, an inhalation powder and an injection. Among them, an injection is preferred since it is not digested more easily than an oral solid preparation, an oral liquid preparation or an inhalation powder is.
<Injection>

The injection is not particularly limited and may be appropriately selected depending on the intended purpose. Examples of the injection include a solution, a suspension and a solid preparation reconstituted upon use.

The method for producing the injection is not particularly limited and may be a routine method. For example, the injection can be produced by adding a pH adjuster, a buffer, a stabilizing agent, a tonicity agent, a local anesthetic, etc. to the phosphorylation inhibitor, the insulin resistance improving agent, or the preventive or therapeutic agent for diabetes. Here, the pH adjuster or buffer is not particularly limited and may be appropriately selected depending on the intended purpose. Examples of the pH adjuster or buffer include sodium citrate, sodium acetate and sodium phosphate. The stabilizing agent is not particularly limited and may be appropriately selected depending on the intended purpose. Examples of the stabilizing agent include sodium pyrosulfite, EDTA, thioglycolic acid and thiolactic acid. The tonicity agent is not particularly limited and may be appropriately selected depending on the intended purpose. Examples of the tonicity agent include sodium chloride and glucose. The local anesthetic is not particularly limited and may be appropriately selected depending on the intended purpose. Examples of the local anesthetic include procaine hydrochloride and lidocaine hydrochloride.
<Administration>

In the phosphorylation inhibitor, the insulin resistance improving agent, or the preventive or therapeutic agent for diabetes, the administration method, the administration dose, the time of administration and the subject to be administered are not particularly limited and may be appropriately selected depending on the intended purpose.

The administration method is not particularly limited and may be appropriately selected depending on the intended purpose. Examples of the administration method include oral administration, inhalation and injection, with injection being preferred. The administration dose is not particularly limited and may be appropriately selected considering various factors of a subject to be administered, such as the age, body weight, constitution, symptom and the presence or absence of administration of a drug containing other active ingredients.

The animal species serving as the subject to be administered is not particularly limited and may be appropriately selected depending on the intended purpose. Examples of the animal species include human, monkey, pig, bovine, sheep, goat, dog, cat, mouse, rat and bird. Among them, they are suitably administered to human.
(Production Method)

The production method for the phosphorylation inhibitor, the insulin resistance improving agent, or the preventive or therapeutic agent for diabetes is not particularly limited and may be appropriately selected depending on, for example, an intended dosage form described above.
(Screening Method)

The disclosed screening method for at least one of the insulin resistance improving agent and the preventive or therapeutic agent for diabetes includes selecting a compound having at least a phosphorylation inhibitory activity and evaluating the compound based on a HOMA-IR value of a diabetes model animal to which the compound has been administered; and, if necessary, further include other steps.
<Selection>

The selection is performed by measuring at least the presence or absence of interaction between STAT3 and ERK2 to select a compound having a phosphorylation inhibitory activity, and includes a mixture preparation step, an antibody reaction step and a screening step.
—Mixture Preparation Step—

The mixture preparation step is a step of preparing a mixture by, for example, mixing together at least a compound, STAT3 whose Ser727 is not phosphorylated, and an enzyme that phosphorylates the STAT3. This step further includes a treatment by which the STAT3 phosphorylation enzyme contained in the mixture is allowed to phosphorylate the Ser727 of the STAT3.
—Mixture—

The mixture contains at least the above compound, the STAT3 whose Ser727 is not phosphorylated, and the enzyme that phosphorylates the STAT3; and, if necessary, further contains other ingredients.
—Compound—

The compound contained in the mixture is not particularly limited and may be appropriately selected depending on the intended purpose. Examples thereof include peptides.

The method for obtaining the compound is not particularly limited and may be appropriately selected depending on the intended purpose. For example, it may be obtained by chemical synthesis or gene recombinant techniques.

The chemical synthesis or gene recombinant technique used for obtaining the compound is not particularly limited and may be appropriately selected depending on the intended purpose from, for example, known methods in the art.

The amount of the compound contained in the mixture is not particularly limited and may be appropriately selected depending on the intended purpose. For example, it is preferably 0.1 mM to 50 mM as a final concentration, more preferably 0.5 mM to 5 mM.

The method for preparing the compound is not particularly limited and may be appropriately selected depending on the intended purpose. Examples thereof include a method in which the compound is prepared using a solution containing dimethylsulfoxide (DMSO).

The final concentration of the DMSO is not particularly limited and may be appropriately selected depending on the intended purpose. It is preferably 1 mM to 100 mM, more preferably 5 mM to 15 mM.

—STAT3—

The method for obtaining the STAT3 whose Ser727 is not phosphorylated (hereinafter may be referred to as "non-phosphorylated STAT3") is not particularly limited and may be appropriately selected depending on the intended purpose. For example, the non-phosphorylated STAT3 may be a commercially available product.

The amount of the non-phosphorylated STAT3 contained in the mixture is not particularly limited and may be appropriately selected depending on the intended purpose. For example, it is preferably 0.01 μg/mL to 0.5 μg/mL as a final concentration, more preferably 0.025 μg/mL to 0.075 μg/mL.

—Enzyme that Phosphorylates STAT3—

The enzyme that phosphorylates the STAT3 refers to an enzyme that phosphorylates the Ser727 of the non-phosphorylated STAT3.

The enzyme that phosphorylates the STAT3 is not particularly limited and may be appropriately selected depending on the intended purpose. For example, it is preferably ERK2 that has been activated through phosphorylation of its Tyr185 (hereinafter may be referred to as "activated ERK2").

The method for obtaining the activated ERK2 is not particularly limited and may be appropriately selected depending on the intended purpose. For example, it may be a commercially available product.

The amount of the activated ERK2 contained in the mixture is not particularly limited and may be appropriately selected depending on the intended purpose. For example, it is preferably 0.0001 μg/mL to 0.015 μg/mL as a final concentration, more preferably 0.0005 μg/mL to 0.005 μg/mL.

—Other Ingredients—

The other ingredients are not particularly limited and may be appropriately selected depending on the intended purpose. Examples thereof include a reaction buffer in which the activated ERK2 can exhibit its enzymatic activity, ATP, magnesium chloride and DMSO.

The composition of the reaction buffer is not particularly limited and may be appropriately selected depending on the intended purpose. The reaction buffer preferably has the following composition: 50 mM tris-HCl (pH 7.5), 10 mM magnesium chloride, 0.02% by mass bovine serum albumin (BSA) and 1 mM dithiothreitol (DTT) (these concentrations are all final concentrations).

The concentration of the ATP is not particularly limited and may be appropriately selected depending on the intended purpose. It is preferably 0.1 mM to 5 mM as a final concentration, more preferably 0.5 mM to 2 mM.

The concentration of the magnesium chloride is not particularly limited and may be appropriately selected depending on the intended purpose. It is preferably 1 mM to 100 mM as a final concentration, more preferably 5 mM to 20 mM.

The concentration of the DMSO is not particularly limited and may be appropriately selected depending on the intended purpose. It is preferably 1% by mass to 25% by mass as a final concentration, more preferably 5% by mass to 22% by mass.

—Preparation of Mixture—

The preparation method for obtaining the mixture is not particularly limited and may be appropriately selected depending on the intended purpose. Examples thereof include a method in which the mixture is suspended with a pipette.

The timing when the compound, the non-phosphorylated STAT3, the enzyme that phosphorylates the STAT3, or the other ingredients are added is not particularly limited. They may be added to the mixture at an appropriate timing during the preparation of the mixture.

—Treatment for Phosphorylation—

The treatment by which the enzyme that phosphorylates the STAT3 is allowed to phosphorylate the Ser727 of the non-phosphorylated STAT3 (hereinafter may be referred to as "phosphorylation treatment") is not particularly limited and may be appropriately selected depending on the intended purpose.

The temperature at the phosphorylation treatment is not particularly limited and may be appropriately selected depending on the intended purpose. It is preferably 20° C. to 30° C.

The period of the phosphorylation treatment is not particularly limited and may be appropriately selected depending on the intended purpose. It is preferably 30 min to 150 min.

The method for terminating the phosphorylation is not particularly limited and may be appropriately selected depending on the intended purpose.

Examples thereof include a method in which ethylenediamine tetraacetate is added to the mixture.

—Antibody Reaction Step—

The antibody reaction step is, for example, a step of reacting the STAT3 whose Ser727 has been phosphorylated in the mixture with an antibody that binds to a phosphorylated site of the STAT3 whose Ser727 has been phosphorylated. This step includes a detection treatment for the bound antibody.

—Antibody that Binds to Phosphorylated Site of Phosphorylated STAT3—

The antibody that binds to the phosphorylated site of the Ser727 of the STAT3 (hereinafter may be referred to as "primary antibody") is not particularly limited, so long as it can recognize the phosphorylated site of the Ser727 of the STAT3, and may be appropriately selected depending on the intended purpose.

The primary antibody is not particularly limited and may be appropriately selected depending on the intended purpose. It may be, for example, anti-pS727 STAT (product of SANTA CRUZ Inc., Cat. No.: sc-21876).

—Reaction—

The reaction is, for example, a reaction for allowing the primary antibody (i.e., the antibody that binds to the phosphorylated site of the Ser727 of the STAT3) to bind to the STAT3 whose Ser727 has been phosphorylated.

The temperature for the reaction between the STAT3 and the primary antibody is not particularly limited and may be appropriately selected depending on the intended purpose. It is preferably 20° C. to 30° C.

The time of the reaction between the STAT3 and the primary antibody is not particularly limited and may be appropriately selected depending on the intended purpose. It is preferably 5 min to 15 min.

Here, the STAT3 with which the primary antibody reacts is the STAT3 in which the phosphorylation site of the Ser727 has been phosphorylated.

—Detection Treatment—

The detection treatment is, for example, a treatment for detecting the reacted STAT3.

The method for detecting the reacted STAT3 is not particularly limited and may be appropriately selected depending on the intended purpose. Examples thereof include a detection method using an antibody that binds specifically to the primary antibody (hereinafter may be referred to as "secondary antibody").

The secondary antibody is not particularly limited and may be appropriately selected depending on the intended purpose. It may be, for example, IgG of a host with which the primary antibody is produced.

Also, the secondary antibody is preferably labeled. The label is not particularly limited and may be appropriately selected depending on the intended purpose. Examples thereof include horseradish peroxidase (HRP).

The method for detecting the HRP is not particularly limited and may be appropriately selected depending on the intended purpose. Examples thereof include a method using a substrate of the HRP.

The substrate of the HRP is not particularly limited and may be appropriately selected depending on the intended purpose. Examples thereof include dimethylformamide (DMF).

—Screening Step—

The screening step is, for example, a step of screening for the compound present in the mixture containing the STAT3 to which the antibody has not bound, as a compound having a phosphorylation inhibitory activity. Specifically, in this step, the presence or absence of the phosphorylation inhibitory activity of the compound is determined and, when the compound has the phosphorylation inhibitory activity, the degree of the phosphorylation inhibitory activity is determined.

The method for the screening is not particularly limited and may be appropriately selected depending on the intended purpose. Examples thereof include a method in which the presence or absence of the phosphorylation inhibitory activity is determined based on the intensity of a band detected through western blotting (i.e., a band of the STAT3 whose Ser727 has been phosphorylated).

The method for determining the presence or absence of the phosphorylation inhibitory activity based on the intensity of the band is not particularly limited and may be appropriately selected depending on the intended purpose. For example, the following method using as a control a mixture that does not contain the compound can be employed. Specifically, by comparing the mixture containing the compound with the control in terms of the band intensity, the compound contained in the mixture whose band is lighter than that of the control is determined as the compound having the phosphorylation inhibitory activity. Alternatively, the following method using no control can be employed. Specifically, by comparing the mixtures containing the compounds with one another in terms of the band intensity, the compound contained in the mixture whose band is lighter than those of the other mixtures is determined as having the phosphorylation inhibitory activity, and this compound is determined as a compound having a higher phosphorylation inhibitory activity.

The method for comparing the band intensities is not particularly limited and may be appropriately selected depending on the intended purpose. Examples thereof include a method in which the bands are visually compared with one another and a method in which the bands are compared with one another using a device such as a densitometer.

<Evaluation>

The evaluation is performed by evaluating whether X>Y where X denotes a HOMA-IR of a diabetes model animal to which the compound has not been administered and Y denotes a HOMA-IR of a diabetes model animal to which the compound has been administered.

The animal species of the diabetes model animal is not particularly limited and may be appropriately selected depending on the intended purpose. Examples thereof include monkey, pig, bovine, sheep, goat, dog, cat, mouse, rat and bird. Among them, mouse is preferred since screening for at least one of the insulin resistance improving agent and the preventive or therapeutic agent for diabetes can easily be performed. The diabetes model mouse is not particularly limited and may be appropriately selected depending on the intended purpose. Examples thereof include db/db mouse (genetically obese mice) (product of Shanghai SLAC Laboratory Animal).

As described above, it can be recognized that the lower the HOMA-IR value is, the more improved the insulin resistance is. Thus, when X>Y as a result of comparison between the HOMA-IR value (X) of the diabetes model mouse to which the compound has not been administered (serving as a control) and the HOMA-IR value (Y) of the diabetes model to which the compound has been administered, the compound can be screened for as at least one of the insulin resistance improving agent and the preventive or therapeutic agent for diabetes. Notably, the HOMA-IR value can be calculated by the above-described HOMA-IR method.

<Other Steps>

The other steps are not particularly limited and may be appropriately selected depending on the intended purpose. In one exemplary step, using as an index other diabetes-related factors and the like, further screening is performed on the compounds having made the HOMA-IR value of the diabetes model mouse lower than the HOMA-IR value (X) of the control in the above evaluation, to thereby select a compound effective as the insulin resistance improving agent and the preventive or therapeutic agent for diabetes.

EXAMPLES

Hereinafter, the examples of the present invention will be specifically explained, but these examples shall not be construed as to limit the scope of the present invention.

Production Example 1

Synthesis of New Compound

The peptide expressed by the following SEQ ID No. 1 was used as the new compound. The peptide expressed by the following SEQ ID No. 1 was chemically synthesized using a peptide synthesizer (product of Shimadzu Corporation).

```
                                            (SEQ ID No. 1)
            Lys-Lys-Tyr-Ile-Leu-Ala-Leu
```

Test Example 1

Phosphorylation Inhibitory Activity

In the below-described manner, the peptide expressed by the above SEQ ID No. 1 was evaluated for phosphorylation inhibitory activity against phosphorylation of Ser727 of STAT3 by ERK2.

<Selection of Compound Having Phosphorylation Inhibitory Activity>

—Mixture Preparation Step—

—Preparation of Reaction Liquid—

The following ingredients were used at a composition indicated in Table 1 to prepare a reaction liquid: 5× reaction buffer (250 mM tris-HCl (pH 7.5), 50 mM magnesium chloride, 0.1% by mass bovine serum albumin (BSA) and 5 mM dithiothreitol (DTT)), Active ERK solution (0.1 mg/mL) (product of Biosource Inc.), STAT3 solution (0.2 mg/mL) (product of Abcam Inc.) and distilled water.

TABLE 1

| Reagents | Amount added (μL) |
|---|---|
| 5 × Reaction buffer | 21 |
| Active ERK solution | 1 |
| STAT3 solution | 25 |
| Distilled water | 13 |
| Total | 60 |

—Preparation of Compound—

The compound used was the peptide chemically synthesized in Production Example 1 (SEQ ID No. 1). Also, 5-iodotubercidin (product of Calbiochem Inc.) was used as a control compound.

The peptide (SEQ ID No. 1) indicated in Production Example 1 was suspended in dimethylsulfoxide (DMSO) so that the final concentration thereof was adjusted to 10 mM.

The 5-iodotubercidin was suspended in DMSO so that the final concentration thereof was adjusted to 5 mM.

—Preparation of Mixture—

A 5×ATP-MgCl$_2$ solution (5 mM ATP, 50 mM magnesium chloride), dimethylsulfoxide (DMSO) and, as the above compound, the peptide (SEQ ID No. 1) or 5-iodotubercidin were added to the above reaction liquid in this order. Furthermore, distilled water was added to the samples so as to appropriately adjust the volume thereof, whereby reaction mixtures were obtained.

Notably, the reaction mixtures each containing neither the peptide (SEQ ID No. 1) nor the 5-iodotubercidin were used as a control.

Each sample was prepared according to the following Table 2.

TABLE 2

| Sample | 1 Control (22% DMSO) | 2 Control (10% DMSO) | 3 1 mM 5-Iodotubercidin (22% DMSO) | 4 1 mM Peptide (10% DMSO) |
|---|---|---|---|---|
| Reaction liquid (μL) | 5 | 5 | 10 | 10 |
| 5 × ATP-MgCl$_2$ solution (μL) | 1.75 | 1.75 | 3.5 | 3.5 |
| DMSO (μL) | 2 | 0.85 | 0 | 0 |
| 10 mM peptide (μL) | — | — | — | 1.75 |
| 5 mM 5-iodotubercidin (μL) | — | — | 4 | — |
| Distilled water (μL) | 0 | 1.15 | 0 | 2.25 |
| Total (μL) | 8.75 | 8.75 | 17.5 | 17.5 |

From Table 2, the final concentration of the STAT3 is about 0.048 μg/mL, the final concentration of Active ERK2 is about 0.001 μg/mL, the final concentration of DMSO is 10% by mass, the final concentration of the peptide is 1 mM and the final concentration of 5-iodotubercidin is 1.14 mM.

Each of the reaction mixtures was incubated at 30° C. for 130 min to allow Active ERK2 to phosphorylate the Ser727 of the STAT3.

After that, to terminate the phosphorylation, 0.5M ethylenediamine tetraacetate (EDTA) was added in an amount of 2.75 μL to the reaction mixtures serving as a control (Table 2: Sample 1 or 2), and was added in an amount of 5.5 μL to the reaction mixture containing the 5-iodotubercidin (Table 2: Sample 3) or the reaction mixture containing the peptide (Table 2: Sample 4).

—Antibody Reaction Step—
—Western Blotting—

Using an aliquot (23 μL) of each of Samples 1 to 4 indicated in Table 2 after completion of the reaction, 4×SDS loading buffer (125 mM tris-HCl (pH 6.8), 4.3% by mass SDS, 30% by mass glycerol, 10% by mass 2-mercaptoethanol and 0.01% by mass bromophenol blue) was added in an amount of 4 μL to the aliquot of the reaction mixture serving as the control (Sample 1 or 2) and was added to in an amount of 8 μL to the aliquot of the reaction mixture containing the 5-iodotubercidin (Sample 3) or the aliquot of the reaction mixture containing the peptide (Sample 4), followed by boiling at 95° C. for 5 min.

Each (15 μL) of the above samples was applied to MULTIGEL (product of Daiichi Kagaku Yakuhin Co., Ltd.), where the sample was electrophoresized for 30 min at a constant current of 30 mA in an electrophoresis buffer (25 mM tris-HCl (pH 8.4), 192 mM L-glysine, 0.1% by mass SDS).

After completion of the electrophoresis, the MULTIGEL was washed with distilled water for 10 min.

The MULTIGEL was sufficiently immersed in a transfer buffer (25 mM tris-HCl, 192 mM L-glysine, 20% by mass methanol). Then, through blotting for 60 min at a constant current of 10 V, the electrophoresized proteins were transferred from the MULTIGEL to a PVDF membrane (Hybond-P, produce of GE Healthcare).

—Primary Antibody Reaction—

The primary antibody reaction was performed as follows using SNAPid (product of Millipore Inc.).

Specifically, skimmed milk (product of Snow Brand Milk Products Co., Ltd.) was suspended in TBS (20 mM tris-HCl (pH 7.5), 140 mM sodium chloride) so as to have a concentration of 0.5% by mass. After the thus-prepared 0.5% by mass skimmed milk (10 mL) had been added to the wells of the SNAPid, the PVDF membrane having the transferred proteins was subjected to blocking while being drawn with a vacuum pump.

Next, 9 μL of anti-pS727 STAT (Cat. No.: sc-21876, product of SANTA CRUZ Inc.) used as the primary antibody was suspended in 3 mL of TBST (20 mM tris-HCl (pH 7.5), 140 mM sodium chloride, 0.05% by mass tween-20). After removal of the blocking solution, the primary antibody was added to the wells, followed by being left to stand still for 10 min, to thereby allow the primary antibody to bind to the STAT3 whose Ser727 had been phosphorylated.

After removal of the solution containing the primary antibody, 10 mL of TBST was added to the wells to wash the unbound primary antibody. The washing of the primary antibody was performed three times.

—Secondary Antibody Reaction—

The secondary antibody reaction was performed as follows using the SNAPid.

First, 16.2 µL of Goat anti-rabbit IgG AP conjugated (product of Calbiochem Inc., Cat. No.: DC06L) used as the secondary antibody was suspended in 3 mL of TBST. After removal of the TBST used for washing the primary antibody, the secondary antibody was added to the wells, followed by being left to stand still for 10 min, to thereby allow the secondary antibody to bind to the primary antibody.

Next, after removal of the solution containing the secondary antibody, 10 mL of TBST was added to the wells to wash the unbound secondary antibody. The washing of the secondary antibody was performed three times.

—Color-Developing Reaction—

The PVDF membrane having undergone the secondary antibody reaction was washed for 5 min with a color-developing buffer (0.1M tris-HCl (pH 9.5), 0.1M sodium chloride, 50 mM magnesium chloride).

Then, the PVDF membrane was immersed in a color-developing reaction liquid (10 mL) for color-developing reaction. After color-developing reaction for several minutes, the color development was visually confirmed, followed by washing with TBST.

Notably, the color-developing reaction liquid was prepared as follows. Specifically, 45 µL of a NBT solution (which had been prepared by suspending 173 mM nitroblue tetrazolium in 70% by mass dimethylformamide) and 35 µL of a BCIP solution (which had been prepared by suspending 250 mg bromochloroindolylphosphate (5-bromo-4-chloro-3-indolyl phosphate) in 5 mL of dimethylformamide (DMF)) were mixed together to obtain the color-developing reaction liquid.

Figure 2:
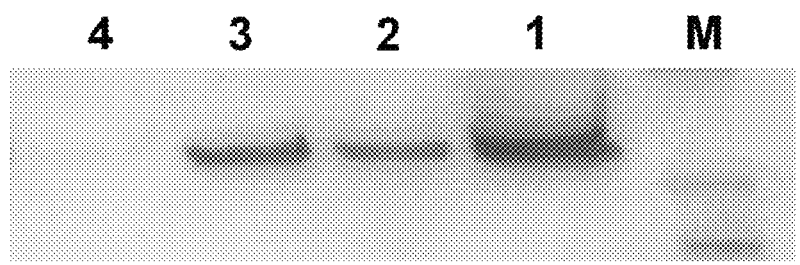
FIG. 2 is an enlarged view of FIG. 1.

The whole image obtained by the western blotting is given in FIG. 1, and the enlarged view of FIG. 1 is given in FIG. 2. In FIGS. 1 and 2, from the right to the left, "M" corresponds to a lane of a molecular-weight marker, "1" corresponds to a lane of Sample 1 serving as a control of the 5-iodotubercidin, "2" corresponds to a lane of Sample 2 serving as a control of the peptide expressed by SEQ ID No. 1, "3" corresponds to a lane of Sample 3 containing the 5-iodotubercidin, and "4" corresponds to a lane of Sample 4 containing the peptide expressed by SEQ ID No. 1.

—Screening Step—

From the result of the western blotting in Test Example 1, the band was detected in the 5-iodotubercidin (Sample 3) but was lower in intensity than the band detected in the control (Sample 1). Thus, it was confirmed that the 5-iodotubercidin had a phosphorylation inhibitory activity. In contrast, no band was detected in the peptide expressed by SEQ ID No. 1 (Sample 4). Thus, it was thought that this peptide had a phosphorylation inhibitory activity higher than that of the 5-iodotubercidin (Sample 3).

Therefore, it was recognized that the peptide expressed by SEQ ID No. 1 was useful as a phosphorylation inhibitor for the phosphorylation of the Ser727 of the STAT3.

Test Example 2

Acute Toxicity Test

The peptide expressed by SEQ ID No. 1 was examined for acute toxicity as follows.
<Test Animal>
—Acclimation—

Fifty-four female db/db mice (body weight: 40 g to 60 g, age: 56 days old to 70 days old, product of Shanghai SLAC Laboratory Animal Inc.) were used as the test animal.

After arrival of the above mice, they were evaluated for general health conditions and acclimated for 7 days before test.

—Breeding—

The mice were kept as a population during acclimation. Then, during their lives, they were individually kept according to the guideline of the U.S. National Research Council "Guide for the Care and Use of Laboratory Animals."

The environment of the animal room was controlled to a temperature of 18° C. to 26° C. and a relative humidity of 30% to 70%. In addition, each of the daytime and the nighttime was controlled to become 12 hours. The temperature and relative humidity were measured every day.

Regarding feeding, feed (product of Shanghai SLAC Laboratory Animal inc., Cat. No.: M-01F) was given to all the test animals ad libitum.

On the previous day before the measurement of the fasting blood glucose level and the blood insulin level, they were fed during a period of 20:30 to 21:00. After the above period had passed, the remaining feed was removed, if any. The fasting period was set to 12 hours to 14 hours, and the test animals were fed after blood sampling. After subjected to high-pressure sterilization, water was given to them ad libitum.

—Selection of Test Animal—

On the basis of the blood glucose levels measured during feeding and fasting, 52 test animals were selected out of the 54 test animals. The test animal exhibiting too high or low a blood glucose level was excluded.

—Clinical Remarks—

Once a day, each of the test animals was confirmed for survival and stool in the morning, and was observed for clinical remarks in the afternoon.

<Acute Toxicity Test>
—Method—

Two individuals of the above mice were used to study the peptide expressed by SEQ ID No. 1 for acute toxicity.

The above peptide was treated in the following manner. Specifically, 8.0 mg of the peptide was dissolved in 0.4 mL of physiological saline to prepare a 20 mg/mL peptide solution (hereinafter may be referred to as "peptide solution 1").

The peptide solution 1 was newly provided before administration, and stirred so that the peptide was dissolved completely and homogeneously.

The above-prepared peptide solution 1 was intraperitoneally injected once to one mouse at a dose of 30 mg/kg and to the other mouse at a dose of 100 mg/kg.

The mice having received the peptide solution 1 were monitored for clinical signs and change in body weight for 14 days. The fasting blood glucose level and fasting blood insulin level were measured on Day 0 and Day 14 by the below-described method.

—Sampling of Blood Sample—

To measure the fasting blood glucose level and blood insulin level, 50 µL of blood was sampled from the postorbital region on Day 0 and Day 14 after administration. To obtain serum, the blood sample was left to stand in a tube on ice and, within 1 hour, the blood sample was centrifuged (5,000 g, 20 min, 2° C. to 8° C.). The fraction obtained through the centrifugation was transferred to a polyethylene microcentrifuge tube, which was stored in a frozen state at −80° C. before analysis.

—Blood Chemical Analysis—

The blood glucose level was determined using Johnson one-touch Ultra Glucose Monitoring System (product of Johnson & Johnson K.K.).

The blood insulin level was determined using a mouse insulin ELISA kit (Cat. #EZRMI-13K, product of Linco Research Inc.).

—Results—

The results of the acute toxicity test are given in the following Table 3.

TABLE 3

| | Day 0 | | | Day 14 | | |
|---|---|---|---|---|---|---|
| Dose (mg/kg) | Body weight (g) | Fasting blood glucose level (mM) | Fasting blood insulin level (ng/mL) | Body weight (g) | Fasting blood glucose level (mM) | Fasting blood insulin level (ng/mL) |
| 30 | 42.53 | 22.7 | 18.78 | 44.6 | 15.3 | 17.68 |
| 100 | 43.36 | 18.3 | 13.95 | 44.5 | 25.3 | 12.85 |

From Table 3, the mouse having received the above peptide solution 1 at a dose of 30 mg/kg or 100 mg/kg exhibited no significant changes in the fasting blood glucose level, the fasting blood insulin level and the body weight. In addition, there were no adverse events observed from the clinical remarks. The fasting blood glucose level and the fasting blood insulin level on Day 0 and Day 14 after administration are given in Table 3.

Test Example 3

Efficacy Test

The compound exhibiting a phosphorylation inhibitory activity in Test Example 1 (i.e., the peptide expressed by SEQ ID No. 1) was evaluated for efficacy as at least one of an insulin resistance improving agent and a preventive or therapeutic agent for diabetes in the following manner.

<Method>

—Test Animal—

Fifty mice described in Test Example 2 were used as a test animal.

—Preparation of Peptide Solution and Metformin Solution—

To study the efficacy of the peptide expressed by SEQ ID No. 1, a peptide solution was prepared as follows.

Specifically, 3.8 mg of the above peptide was dissolved in 4.75 mL of physiological saline to prepare a 0.8 mg/mL peptide solution (hereinafter may be referred to as "peptide solution 2"). Then, 1.75 mL of the peptide solution 2 was dissolved in 3.5 mL of physiological saline to prepare a 0.27 mg/mL peptide solution (hereinafter may be referred to as "peptide solution 3"). Further, 1 mL of the peptide solution 3 was dissolved in 2 mL of physiological saline to prepare a 0.09 mg/mL peptide solution (hereinafter may be referred to as "peptide solution 4").

A metformin solution used for an activity control group was prepared as follows. Specifically, 120 mg of metformin (product of Sigma Co.) was dissolved in 4 mL of physiological saline to prepare a 30 mg/mL metformin solution.

Each of the peptide solutions 2 to 4 and the metformin solution was newly provided before administration and stirred so that the peptide or metformin was dissolved completely and homogeneously.

—Administration—

The efficacy test was conducted using the following five administration groups: a solvent (physiological saline) control administration group, a 150 mg/kg metformin administration group (serving as an activity control group), a 4.00 mg/kg peptide (expressed by SEQ ID No. 1) administration group, a 1.33 mg/kg peptide administration group and a 0.44 mg/kg peptide administration group. Each administration group had 10 mice.

The above-prepared metformin solution was used for the 150 mg/kg metformin administration group, the peptide solution 2 was used for the 4.00 mg/kg peptide administration group, the peptide solution 3 was used for the 1.33 mg/kg peptide administration group, and the peptide solution 4 was used for the 0.44 mg/kg peptide administration group.

The appropriate dose of metformin administered to human is 750 mg/day. This dose was converted based on the body weight of mouse, and metformin was administered to the mice at an excessive amount of 150 mg/kg.

The above-prepared solutions were intraperitoneally injected every day to all of the mice of the test groups at the corresponding doses given in the following Table 4 for 28 days. The body weight, the fasting blood glucose level, the postprandial blood glucose level and the fasting blood insulin level were measured by the below-described measuring method according to the measurement schedule given in the following Table 5.

Notably, as indicated in Table 6, the above 50 mice were divided into five administration groups so that the distribution of each of the fasting blood glucose level, the fasting blood insulin level and the HOMA-IR value (index of insulin resistance) (measured on Day 0) became equal between the administration groups. The calculating method for the HOMA-IR value is described below.

Figure 3:
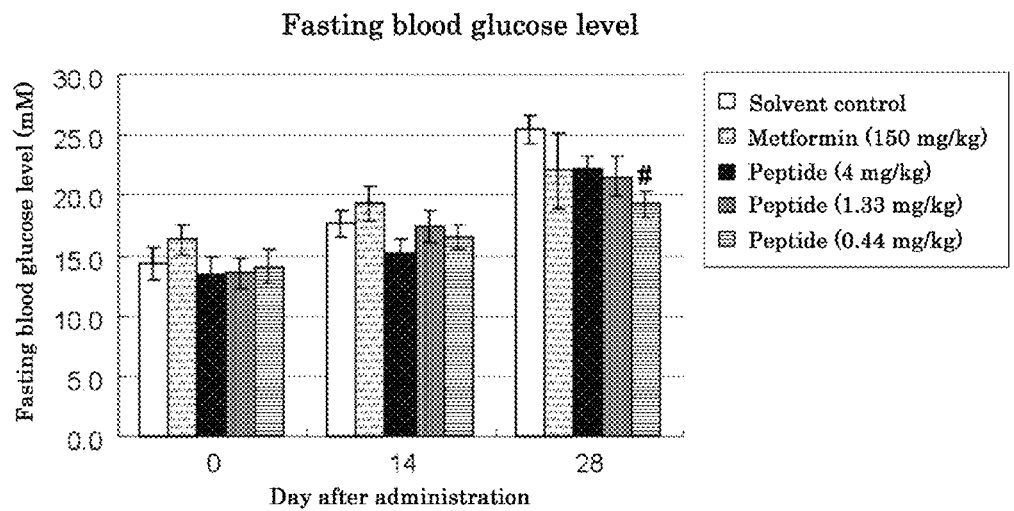
FIG. 3 is a graph of the fasting blood glucose levels measured in an efficacy test on Day 0, Day 14 and Day 28 after administration, wherein the five bars corresponding to each day indicate, from the left to the right, a bar for a solvent control group, a bar for a 150 mg/kg metformin administration group, a bar for a 4.00 mg/kg peptide administration group, a bar for a 1.33 mg/kg peptide administration group and a bar for a 0.44 mg/kg peptide administration group.

FIG. 3 gives the fasting blood glucose level on Day 0 in each administration group.

Figure 5:
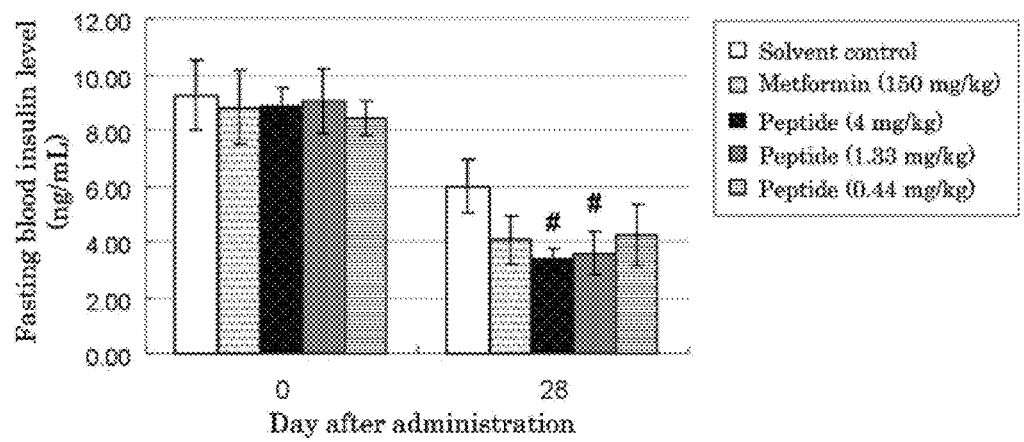
FIG. 5 is a graph of the fasting blood insulin levels measured in an efficacy test on Day 0 and Day 28 after administration, wherein the five bars corresponding to each day indicate, from the left to the right, a bar for a solvent control group, a bar for a 150 mg/kg metformin administration group, a bar for a 4.00 mg/kg peptide administration group, a bar for a 1.33 mg/kg peptide administration group and a bar for a 0.44 mg/kg peptide administration group.

FIG. 5 gives the fasting blood insulin level on Day 0 in each administration group.

Figure 6:
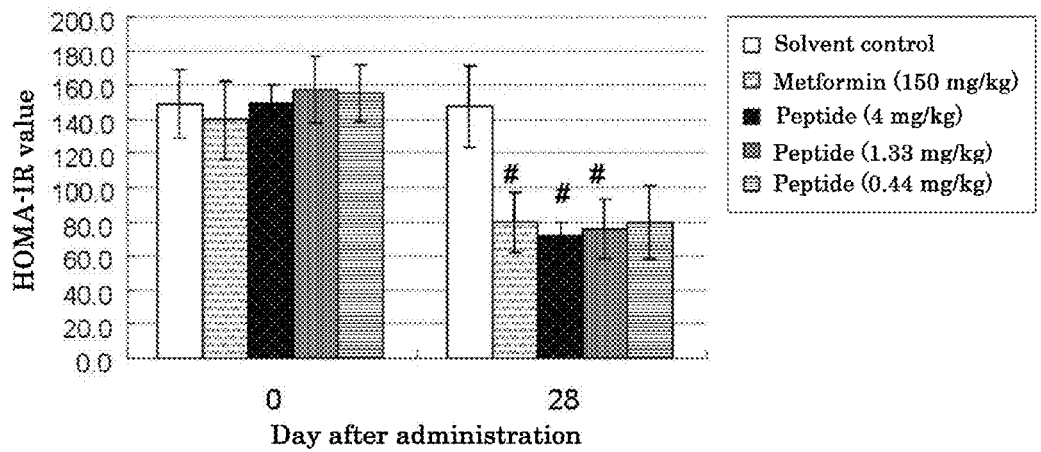
FIG. 6 is a graph of the HOMA-IR values measured in an efficacy test on Day 0 and Day 28 after administration, wherein the five bars corresponding to each day indicate, from the left to the right, a bar for a solvent control group, a bar for a 150 mg/kg metformin administration group, a bar for a 4.00 mg/kg peptide administration group, a bar for a 1.33 mg/kg peptide administration group and a bar for a 0.44 mg/kg peptide administration group.

FIG. 6 gives the HOMA-IR value on Day 0 in each administration group.

—Sampling of Blood Sample—

To measure the fasting blood glucose level and blood insulin level, 50 µL of blood was sampled from the postorbital region on Day 0, Day 14 and Day 28 after administration. The serum was obtained in the same manner as in Test Example 2.

The postprandial blood glucose level was measured using blood sampled from the tail vein on Day 1, Day 13, and Day 27 after administration.

—Blood Chemical Analysis—

The blood glucose level and blood insulin level were measured in the same manner as in Test Example 2.

The insulin resistance was determined by the HOMA (homeostasis model assessment) method using the following calculation formula.

$$\text{HOMA-IR (index of insulin resistance)} = \text{fasting insulin level (µU/mL)} \times \text{fasting blood glucose level (mmol/L)}/22.5$$

Here, it can be recognized that the lower the HOMA-IR value is, the more improved the insulin resistance is (see Matthews D R et al., Diabetologia 1985 July 28(7), 412-9, Kanauchi M et al., Diabetes Care, October 25(10), 2002, p. 1891-2).

—Numerical Analysis—

All of the values are indicated as "average value±average error." The important differences between the groups and within each group were evaluated through one-way variance analysis and Dunnett's multiple comparison. The p-values equal to or lower than 0.05 were regarded as statistically significant.

TABLE 4

| Test group | Number/Sex | Administration method | Dose (mg/kg) | Volume administered (mL/kg) | Administration concentration (mg/mL) |
|---|---|---|---|---|---|
| Solvent control | 10/Female | Intraperitoneal injection | NA | 5 | NA |
| Metformin (150 mg/kg) | 10/Female | Intraperitoneal injection | 150 | 5 | 1.00 |
| Peptide (4.00 mg/kg) | 10/Female | Intraperitoneal injection | 4.00 | 5 | 0.80 |
| Peptide (1.33 mg/kg) | 10/Female | Intraperitoneal injection | 1.33 | 5 | 0.27 |
| Peptide (0.44 mg/kg) | 10/Female | Intraperitoneal injection | 0.44 | 5 | 0.09 |

TABLE 5

| Measurement method | Measurement days |
|---|---|
| Body weight | 0, 7, 14, 21, 28 |
| Fasting blood glucose level | 0, 14, 28 |
| Postprandial blood glucose level | 1, 13, 27 |
| Fasting blood insulin level | 0, 28 |

TABLE 6

| Test group | Fasting blood glucose level (mM) | Postprandial blood glucose level (mM) | Fasting blood insulin level (ng/mL) | HOMA-IR value |
|---|---|---|---|---|
| Solvent control | 14.4 ± 1.3 | 18.2 ± 1.9 | 9.23 ± 1.26 | 149.0 ± 20.0 |
| Metformin (150 mg/kg) | 16.3 ± 1.3 | 22.5 ± 2.0 | 8.81 ± 1.33 | 139.4 ± 22.7 |
| Peptide (4.00 mg/kg) | 13.5 ± 1.5 | 23.0 ± 1.7 | 8.87 ± 0.69 | 149.1 ± 11.5 |
| Peptide (1.33 mg/kg) | 13.6 ± 1.2 | 22.4 ± 1.6 | 9.05 ± 1.17 | 157.4 ± 19.2 |
| Peptide (0.44 mg/kg) | 14.1 ± 1.4 | 22.9 ± 1.5 | 8.45 ± 0.6 | 155.6 ± 16.6 |

<Results>

The following Table 7 gives the postprandial blood glucose levels measured on Day 13 after administration and the fasting blood glucose levels measured on Day 14.

Figure 4:
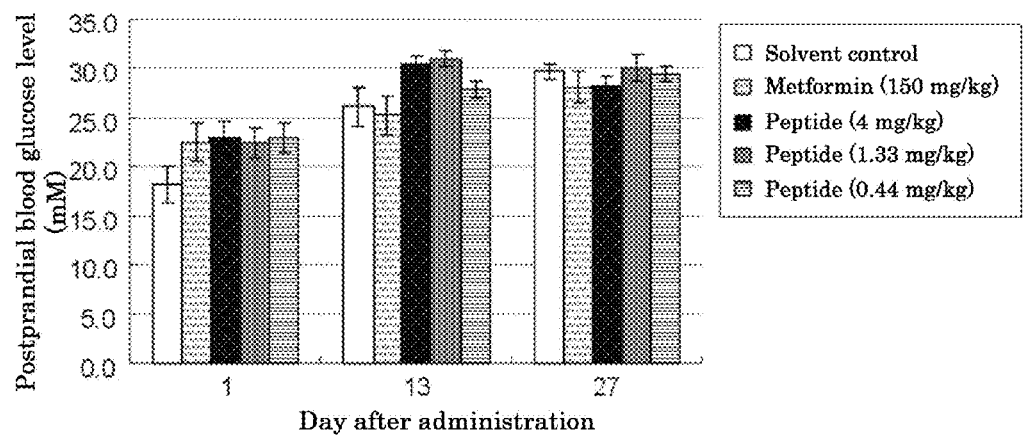
FIG. 4 is a graph of the postprandial blood glucose levels measured in an efficacy test on Day 1, Day 13 and Day 27 after administration, wherein the five bars corresponding to each day indicate, from the left to the right, a bar for a solvent control group, a bar for a 150 mg/kg metformin administration group, a bar for a 4.00 mg/kg peptide administration group, a bar for a 1.33 mg/kg peptide administration group and a bar for a 0.44 mg/kg peptide administration group.

FIG. 4 gives the postprandial blood glucose levels measured on Day 13 after administration in each administration group.

FIG. 3 gives the fasting blood glucose levels measured on Day 14 after administration in each administration group.

TABLE 7

| Test group | Fasting blood glucose level (mM) | Postprandial blood glucose level (mM) |
|---|---|---|
| Solvent control | 17.6 ± 1.1 | 26.1 ± 2.0 |
| Metformin (150 mg/kg) | 19.3 ± 1.5 | 25.2 ± 2.0 |
| Peptide (4.00 mg/kg) | 15.2 ± 1.2 | 30.3 ± 0.9 |
| Peptide (1.33 mg/kg) | 17.4 ± 1.3 | 31.0 ± 0.7 |
| Peptide (0.44 mg/kg) | 16.5 ± 1.1 | 27.9 ± 0.8 |

The following Table 8 gives the HOMA-IR values calculated from the postprandial blood glucose levels measured on Day 27 after administration and the fasting blood glucose levels and the fasting blood insulin levels measured on Day 28 after administration.

FIG. 4 gives the postprandial blood glucose levels measured on Day 27 after administration in each administration group.

FIG. 3 gives the fasting blood glucose levels measured on Day 28 after administration in each administration group.

FIG. 5 gives the fasting blood insulin levels measured on Day 28 after administration in each administration group.

FIG. 6 gives the fasting HOMA-IR values measured on Day 28 after administration in each administration group.

Notably, "#" in FIGS. 3, 5 and 6 means that the values indicated thereby are statistically significant with respect to the solvent control group as a result of the numerical analysis.

TABLE 8

| Test group | Fasting blood glucose level (mM) | Postprandial blood glucose level (mM) | Fasting blood insulin level (ng/mL) | HOMA-IR value |
|---|---|---|---|---|
| Solvent control | 22.5 ± 1.2 | 29.7 ± 0.8 | 6.00 ± 0.98 | 147.3 ± 23.6 |
| Metformin (150 mg/kg) | 22.0 ± 3.1 | 28.1 ± 1.6 | 4.06 ± 0.84 | 79.6 ± 17.7[#] |
| Peptide (4.00 mg/kg) | 22.3 ± 1.0 | 28.3 ± 1.0 | 3.36 ± 0.41[#] | 71.4 ± 8.6[#] |
| Peptide (1.33 mg/kg) | 21.5 ± 1.7 | 30.1 ± 1.3 | 3.59 ± 0.79[#] | 76.1 ± 17.3[#] |
| Peptide (0.44 mg/kg) | 19.3 ± 1.1[#] | 29.4 ± 0.8 | 4.23 ± 1.12 | 79.8 ± 21.4 |

[#]$p < 0.05$ vs. solvent control group

The difference between the fasting blood glucose levels, the postprandial blood glucose levels or the fasting blood insulin levels measured on Day 28 and Day 0 after administration was calculated from the following calculation formulas as an increment of each level. The results are given in the following Table 9.

Increment in fasting blood glucose level=fasting blood glucose level on Day 28—fasting blood glucose level on Day 0

Increment in postprandial blood glucose level=postprandial blood glucose level on Day 28—postprandial blood glucose level on Day 0

Increment in fasting blood insulin level=fasting insulin level on Day 28—fasting insulin level on Day 0

Figure 7:
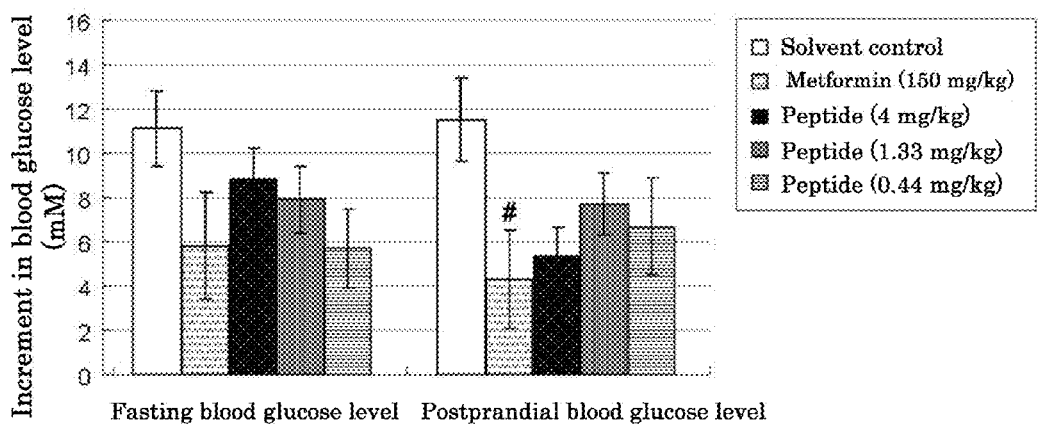
FIG. 7 is a graph of increments of the blood glucose levels measured in an efficacy test, wherein the five bars corresponding to each day after administration indicate, from the left to the right, a bar for a solvent control group, a bar for a 150 mg/kg metformin administration group, a bar for a 4.00 mg/kg peptide administration group, a bar for a 1.33 mg/kg peptide administration group and a bar for a 0.44 mg/kg peptide administration group.

FIG. 7 gives the increments in fasting blood glucose level and postprandial blood glucose level in each administration group.

Figure 8:
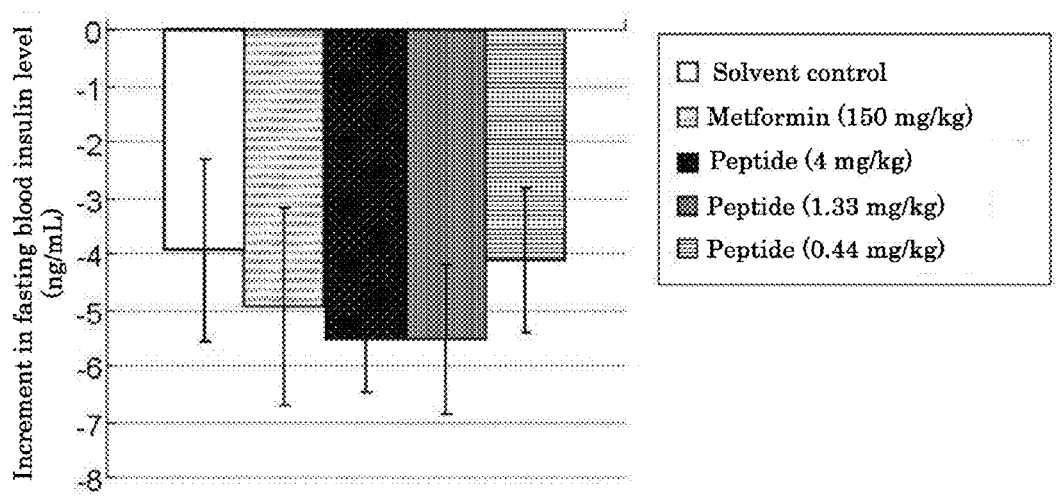
FIG. 8 is a graph of increments of the fasting blood insulin levels measured in an efficacy test, wherein the five bars corresponding to each day after administration indicate, from the left to the right, a bar for a solvent control group, a bar for a 150 mg/kg metformin administration group, a bar for a 4.00 mg/kg peptide administration group, a bar for a 1.33 mg/kg peptide administration group and a bar for a 0.44 mg/kg peptide administration group.

FIG. 8 gives the increment in fasting blood insulin level in each administration group.

Notably, "#" in FIG. 7 means that the value indicated thereby is statistically significant with respect to the solvent control group as a result of the numerical analysis.

TABLE 9

| Test group | Increment in fasting blood glucose level (mM) | Increment in postprandial blood glucose level (mM) | Increment in fasting blood insulin level (ng/mL) |
|---|---|---|---|
| Solvent control | 11.1 ± 1.7 | 11.5 ± 1.9 | −3.94 ± 1.64 |
| Metformin (150 mg/kg) | 5.8 ± 2.4 | 4.3 ± 2.2# | −4.94 ± 1.77 |
| Peptide (4.00 mg/kg) | 8.8 ± 1.4 | 5.3 ± 1.4 | −3.51 ± 0.96 |
| Peptide (1.33 mg/kg) | 7.9 ± 1.5 | 7.7 ± 1.4 | −5.52 ± 1.33 |
| Peptide (0.44 mg/kg) | 5.7 ± 1.8 | 6.7 ± 2.2 | −4.12 ± 1.3 |

$p < 0.05$ vs. solvent control group

As indicated in Tables 6 to 9, the increment of the fasting blood glucose level in the solvent control group was 11.1±1.7 mM, while the increment of the fasting blood glucose level in the 150 mg/kg metformin administration group was 5.8±2.4 mM. Thus, metformin suppressed increase in fasting blood glucose level from Day 0 to Day 28 (Table 9, FIG. 7). However, the suppression of increase in fasting blood glucose level in the 150 mg/kg metformin administration group was not statistically significant.

Meanwhile, the fasting blood insulin level measured on Day 28 after administration decreased in the 150 mg/kg metformin administration group (Table 8, FIG. 5), resulting in that the HOMA-IR value (index of insulin resistance) was significantly decreased (Table 8, FIG. 6).

Also in the administration groups of the peptide expressed by SEQ ID No. 1, similar to metformin, the suppressions of increase in fasting blood glucose level were not statistically significant for a test period of 28 days (Table 9, FIG. 7). However, in each of the 1.33 mg/kg peptide administration group and the 4.00 mg/kg peptide administration group, the fasting blood insulin level (Table 8, FIG. 5) and the HOMA-IR value (Table 8, FIG. 6) measured on Day 28 after administration significantly decreased as compared with the solvent control group.

Also, in the administration groups of the peptide expressed by SEQ ID No. 1, the fasting blood insulin level and the HOMA-IR level decreased in a dose-dependent manner (Table 8).

Furthermore, although the dose of the 1.33 mg/kg peptide administration group or the 4.00 mg/kg peptide administration group was lower than that of the 150 mg/kg metformin administration group, the fasting blood insulin level and the HOMA-IR level decreased as compared with the 150 mg/kg metformin administration group (Table 8, FIGS. 5 and 6).

These results indicate that the peptide expressed by SEQ ID No. 1 is effective as at least one of an insulin resistance improving agent and a preventive or therapeutic agent for diabetes.

Also, since the effective concentration of the peptide expressed by SEQ ID No. 1 is lower than that of the existing drug metformin, the peptide is advantageously used as at least one of an insulin resistance improving agent and a preventive or therapeutic agent for diabetes.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification related to a showing of the superiority and inferiority of the invention. Although the embodiments of the present invention have been described in detail, it should be understood that the various changes, substitutions, and alterations could be made hereto without departing from the spirit and scope of the invention.

INDUSTRIAL APPLICABILITY

First, the disclosed new compound inhibits phosphorylation of Ser727 of STAT3 to exhibit an excellent phosphorylation inhibitory activity against phosphorylation of Ser727 of STAT3, and thus can suitably be used as a phosphorylation inhibitor for Ser727 of STAT3. In addition, the phosphorylation inhibitor has a target molecule and mechanism which are for reducing the blood glucose level of patients with diabetes and which are different from those of existing drugs, and thus is useful as a preventive or therapeutic agent for insulin resistance, diabetes, obesity, abnormal lipid metabolism, high blood pressure and other pathological conditions. The phosphorylation inhibitor is useful not only as a drug but also as a reagent for assay using phosphorylation as an index.

Second, the disclosed screening method can suitably used for screening for at least one of the insulin resistance improving agent and the preventive or therapeutic agent for diabetes.

What is claimed is:

1. A screening method for at least one of an insulin resistance improving agent and a therapeutic agent for diabetes, the screening method comprising:

determining the presence or absence of interaction between signal transducer and activator of transcription 3 (STAT3) and extracellular signal-regulated kinase 2 (ERK2) to select a compound having a phosphorylation inhibitory activity, and evaluating the compound for whether X>Y where X denotes a Homeostasis model assessment-Insulin Resistance (HOMA-IR) value of a diabetes model animal to which the compound has not been administered and Y denotes a HOMA-IR value of a diabetes model animal to which the compound has been administered, wherein the determining is performed by preparing a mixture by mixing together at least the compound, the STAT3 whose Ser727 is not phosphorylated, and an enzyme that phosphorylates the STAT3; reacting the STAT3 whose Ser727 has been phosphorylated in the mixture with an antibody that binds to a phosphorylated site of the STAT3 whose Ser727 has been phosphorylated; and screening for the compound present in the mixture containing the STAT3 to which the antibody has not bound, as a compound having the phosphorylation inhibitory activity.

2. The screening method according to claim 1, wherein the preparing comprises phosphorylating the Ser727 of the STAT3 contained in the mixture.

3. The screening method according to claim 1, wherein the reacting comprises detecting the antibody binding to the phosphorylated site of the STAT3 whose Ser727 has been phosphorylated.

4. The screening method according to claim 3, wherein the detecting is performed with IgG derived from a host of the antibody binding to the phosphorylated site of the STAT3 whose Ser727 has been phosphorylated.

5. The screening method according to claim 4, wherein the IgG is detected with a label bound thereto.

6. The screening method according to claim 1, wherein the screening is performed by determining the presence or absence of the phosphorylation inhibitory activity of the compound.

* * * * *